(12) United States Patent
Casas et al.

(10) Patent No.: US 10,737,006 B2
(45) Date of Patent: *Aug. 11, 2020

(54) FIDUCIAL POINT OPTIMIZATION

(71) Applicant: HeartWare, Inc., Miami Lakes, FL (US)

(72) Inventors: Fernando Casas, Miami Lakes, FL (US); Justin Wolman, Aventura, FL (US); Carlos Reyes, Davie, FL (US); Antonio Luiz Silva Ferreira, Davie, FL (US)

(73) Assignee: HeartWare, Inc., Miami Lakes, FL (US)

( * ) Notice: Subject to any disclaimer, the term of this patent is extended or adjusted under 35 U.S.C. 154(b) by 130 days.

This patent is subject to a terminal disclaimer.

(21) Appl. No.: 16/124,944

(22) Filed: Sep. 7, 2018

(65) Prior Publication Data
US 2019/0001036 A1    Jan. 3, 2019

Related U.S. Application Data

(63) Continuation of application No. 15/599,115, filed on May 18, 2017, now Pat. No. 10,080,829, which is a
(Continued)

(51) Int. Cl.
*A61M 1/10*    (2006.01)
*A61M 1/12*    (2006.01)

(52) U.S. Cl.
CPC ........ *A61M 1/1086* (2013.01); *A61M 1/1046* (2013.01); *A61M 1/101* (2013.01);
(Continued)

(58) Field of Classification Search
CPC .. A61M 1/101; A61M 1/1031; A61M 1/1046; A61M 1/1086; A61M 1/122;
(Continued)

(56) References Cited

U.S. PATENT DOCUMENTS

| 2004/0039243 A1 | 2/2004 | Bearnson et al. |
| 2007/0100196 A1 | 5/2007 | LaRose et al. |

(Continued)

FOREIGN PATENT DOCUMENTS

| CN | 1638824 A | 7/2005 |
| CN | 103328018 A | 9/2013 |

OTHER PUBLICATIONS

International Search Report and Written Opinion for Application No. PCT/US2015/062430 dated Mar. 7, 2016, 11 pages.
(Continued)

*Primary Examiner* — George Manuel
(74) *Attorney, Agent, or Firm* — Christopher & Weisberg, P.A.

(57) ABSTRACT

A flow rate of blood through an implantable blood pump is determined based on a parameter related to the flow, such as a parameter related to thrust on the rotor of the pump. An amount of current supplied to the pump is used to determine each of a first flow rate value and second flow rate values. Each of the first and second flow rate values, in combination with the parameter related to thrust on the rotor of the pump, are used to calculate a flow rate of blood through the pump.

12 Claims, 10 Drawing Sheets

Related U.S. Application Data continuation of application No. 14/950,213, filed on Nov. 24, 2015, now Pat. No. 9,675,742.

(60) Provisional application No. 62/084,742, filed on Nov. 26, 2014.

(52) U.S. Cl.
CPC ........... *A61M 1/1031* (2014.02); *A61M 1/122* (2014.02); *A61M 2205/3334* (2013.01); *A61M 2205/3365* (2013.01); *A61M 2205/50* (2013.01); *A61M 2205/702* (2013.01)

(58) Field of Classification Search
CPC .. A61M 2205/3334; A61M 2205/3365; A61M 2205/50; A61M 2205/702
See application file for complete search history.

(56) References Cited

U.S. PATENT DOCUMENTS

| | | |
|---|---|---|
| 2007/0119246 A1 | 5/2007 | Miyakoshi et al. |
| 2010/0038317 A1* | 2/2010 | Bissler .................... A61M 1/16 210/650 |
| 2011/0237863 A1 | 9/2011 | Ricci et al. |
| 2012/0245681 A1 | 9/2012 | Casas et al. |
| 2013/0030240 A1 | 1/2013 | Schima et al. |
| 2014/0200390 A1 | 7/2014 | Yanai et al. |

OTHER PUBLICATIONS

China National Intellectual Property Administration, Notice on the First Office Action and Search Report, for corresponding Chinese Application No. 201580074531.8, dated Aug. 14, 2019, 20 pages.

* cited by examiner

FIDUCIAL POINT OPTIMIZATION

CROSS-REFERENCE TO RELATED APPLICATION

This application is a continuation of patent application Ser. No. 15/599,115, filed May 18, 2017 and is a continuation of patent application Ser. No. 14/950,213, filed Nov. 24, 2015, now U.S. Pat. No. 9,675,742 issued Jun. 13, 2017, entitled FIDUCIAL POINT OPTIMIZATION, and is related to and claims priority to U.S. Provisional Application No. 62/084,742, filed Nov. 26, 2014, entitled FIDUCIAL POINT OPTIMIZATION, the entirety of which is incorporated herein by reference.

STATEMENT REGARDING FEDERALLY SPONSORED RESEARCH OR DEVELOPMENT n/a

TECHNICAL FIELD

The present invention relates to blood pumps, to methods of using blood pumps, and to control circuits adapted for use with blood pumps.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD." Where a VAD is used to assist the pumping action of the left ventricle, the device draws blood from the left ventricle of the heart and discharges the blood into the aorta.

To provide clinically useful assistance to the heart, blood pumps must impel blood at a substantial blood flow rate. For an adult human patient, a ventricular assist device may be arranged to pump blood at about 1-10 liters per minute at a pressure differential across the pump of about 10-110 mmHg, depending on the needs of the patient. The needs of the patient may vary with age, height, and other factors.

It is desirable to monitor the rate at which blood is impelled by a blood pump. For example, if a VAD is operated at a flow rate in excess of the inflow rate of blood to the ventricle, the VAD will create a suction condition within the ventricle, wherein the ventricle is collapsed and essentially devoid of blood. This condition is undesirable. In this condition, the flow rate through the pump will decline rapidly. Likewise, if the intake or outlet of the pump is occluded, the flow rate will decline gradually. If the flow rate through the pump declines, either rapidly (e.g., as a result of suction condition) or gradually (e.g., as a result of an obstruction or occlusion) to the extent that the flow rate is insufficient, the device will not provide sufficient circulatory assistance to the patient. Excessive flow also can create undesirable conditions. Therefore, it would be desirable to provide a blood pump controller which can monitor the blood flow rate produced by the blood pump which it controls.

Furthermore, it is preferable to minimize or reduce any errors in the blood flow monitoring process in order to obtain a more accurate estimation of blood flow in the pump. The relationships between certain properties of the pump (e.g., electrical current supplied to the pump, the speed of rotation of a rotor of the pump, etc.) may be generally known and used to predict blood flow rate in the blood pump, such as in the manner described in co-owned U.S. Published Patent Application No. 2012/0245681, entitled "Flow Estimation in a Blood Pump," the disclosure of which is incorporated herein in its entirety. However, these relationships are generally estimated, approximated, or otherwise derived from analogous blood pump devices, and in reality may vary from pump to pump. Inaccuracies in the modeling of a pump's characteristic can in turn lead to inaccuracies in the modeling of flow estimation behavior for the pump, which in turn may lead to a poor blood flow estimation. Therefore, it is further desirable to provide a blood pump monitoring system that is capable of optimizing the parameters that are used to determine blood flow in the pump, thereby minimizing or reducing, errors in the blood flow monitoring process.

SUMMARY

One aspect of the disclosure provides for a method for monitoring operation of an implantable blood pump, involving, determining an amount of current supplied to the pump, determining a first flow rate value and a second flow rate value based on the amount of current supplied to the pump, and determining a flow rate of blood based on a combination of the first and second flow rate values and a weighting parameter such that the combination of the first and second flow rate values varies depending on the weighting parameter. The weighting parameter may increase or decrease monotonically over the range of operable flow rates for the pump, or over a subset of the range of operable flow rates for the pump. A weight may be determined and assigned to each of the first and second flow rate values based at least in part on a relationship between the weighting parameter and a predetermined threshold value. The assigned weight for the first flow rate value may be inversely proportionate to the relationship between the weighting parameter and the predetermined threshold value, and the assigned weight for the second flow rate value may be proportionate to the relationship between the weighting parameter and the predetermined threshold value.

Determining the relationship between the weighting parameter and the predetermined threshold value may involve comparing the difference between the weighting parameter and the threshold value to a preselected spread value. For example, an absolute difference between the weighting parameter and a predetermined threshold value may be calculated, and the absolute difference may be compared to a predetermined spread value. In such an example, determination of the flow rate of blood based on a combination of the first and second flow rate may be limited to when the absolute difference between the third parameter and a predetermined threshold value is less than the predetermined spread value. For instance, if the absolute difference is greater than the spread value, and the third parameter is less than the predetermined threshold value, the flow rate of blood may be determined based on the first flow rate value and not the second flow rate value. Additionally, or alternatively, if the absolute difference is greater than the spread value, and the third parameter is greater than the predetermined threshold value, the flow rate of blood may be determined based on the second flow rate value and not the first flow rate value. Similarly, if the absolute difference is greater than the spread value, the third parameter is less than the predetermined threshold value, and a determined speed of rotation of the rotor is greater than a threshold speed value to which the determined speed is compared, the flow rate of blood may be determined based on the first flow rate value; but if the determined speed is less than the threshold speed value, the flow rate of blood may be determined based on the third parameter and neither of the first and second flow rate values.

In some examples, the implantable blood pump may include a housing having an axis and a rotor disposed within the housing and rotatable around the axis. The weighting parameter may be related to thrust on the rotor along the axis.

Another aspect of the present disclosure provides for a control circuit for monitoring the operation of an implantable blood pump. The control circuit may include a current determination circuit operative to determine an amount of current supplied to the pump, a flow rate value determination circuit operative to determine a first flow rate value and a second flow rate value based on the amount of current supplied to the pump, a transformation circuit operative to determine a weighting parameter, and a flow rate determination circuit operative to determine a flow rate of blood through the pump based on a combination of the first and second flow rate values and the weighting parameter.

Yet another aspect of the present disclosure provides for an implantable blood pump system including a pump with a housing having an axis, and a rotor disposed within the housing, the rotor being rotatable around the axis, and further including the above described control circuit operatively coupled to the pump. The pump may further include a stator operatively coupled to the control circuit. The stator may incorporate a plurality of coils for applying a rotating magnetic field to the rotor, and the weighting parameter may be based on back electromotive force (BEMF) in one or more of the plurality of coils.

Yet a further aspect of the present disclosure provides for a method of optimizing an estimate of flow rate of blood through an implantable blood pump. The method may involve measuring the flow rate of blood through the implantable blood pump, estimating the flow rate of blood through the implantable blood pump based at least in part on a first parameter related to thrust on the rotor along the axis and a second parameter selected from one of a threshold value and a spread value, determining a difference between the measured flow rate and the estimated flow rate, and adjusting the second parameter based on the determined difference such that estimating the flow rate of blood based on the adjusted second parameter results in a reduced difference between the measured flow rate and the estimated flow rate. The estimating, determining, adjusting, and optionally measuring, steps may continue repeatedly only if the determined difference between the measured flow rate and the estimated flow rate is not less than a threshold error value.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
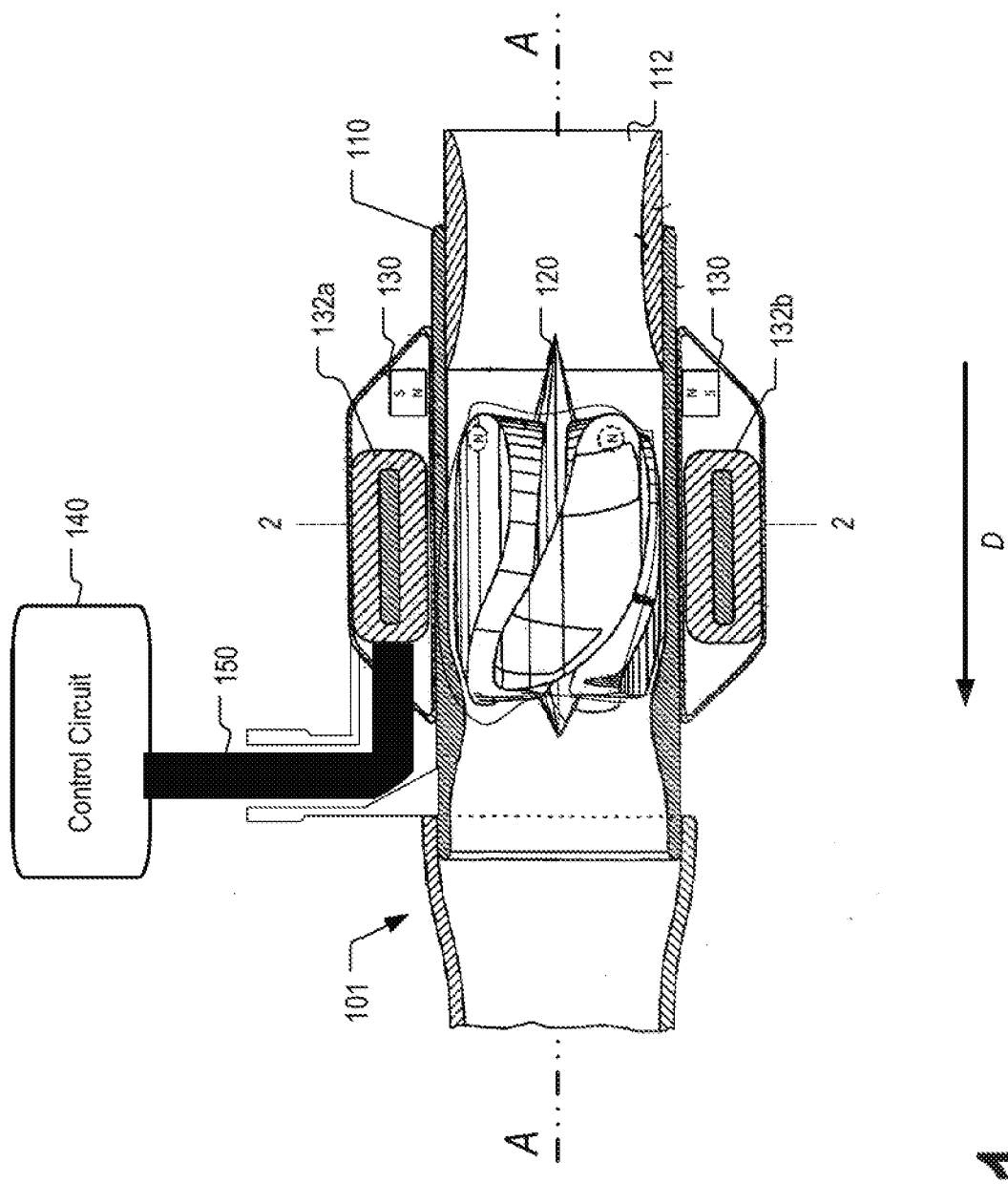
FIG. 1 is a schematic, partially sectional view of a blood pump system in accordance with one embodiment of the invention.
Figure 2:
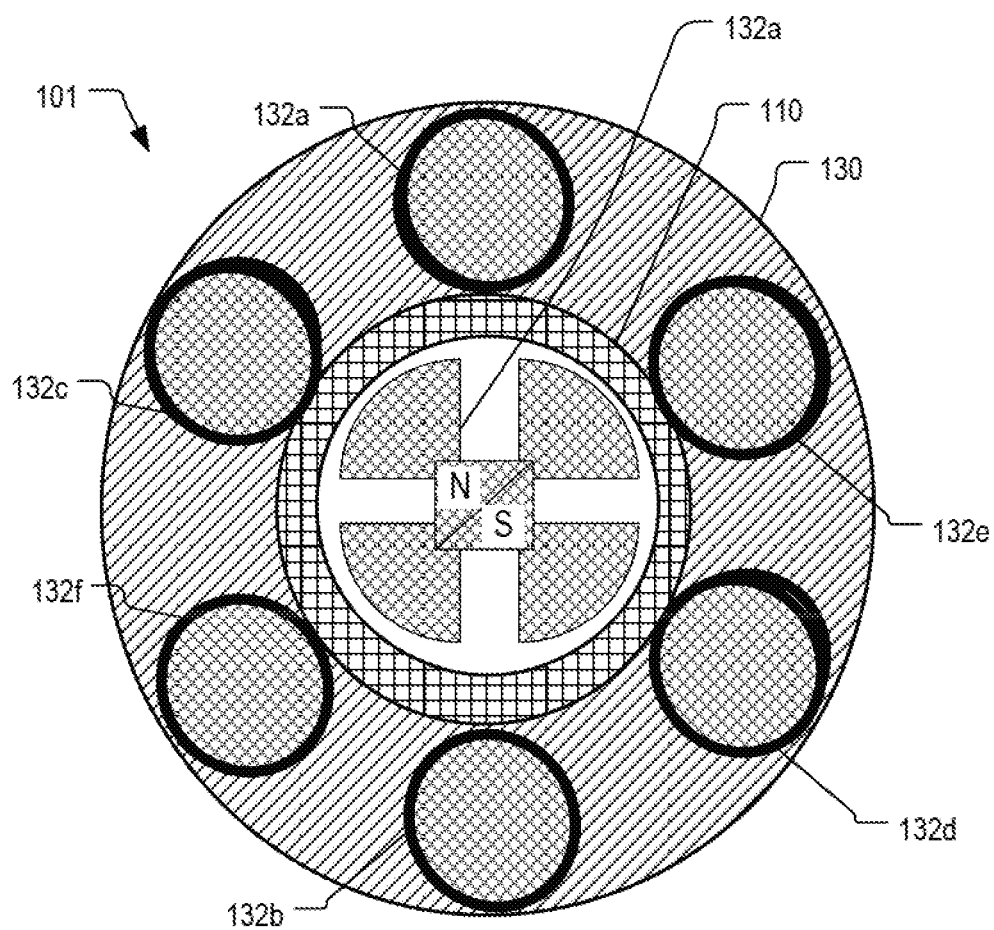
FIG. 2 is a diagrammatic sectional view taken along line 2-2 in FIG. 1.
Figure 3:
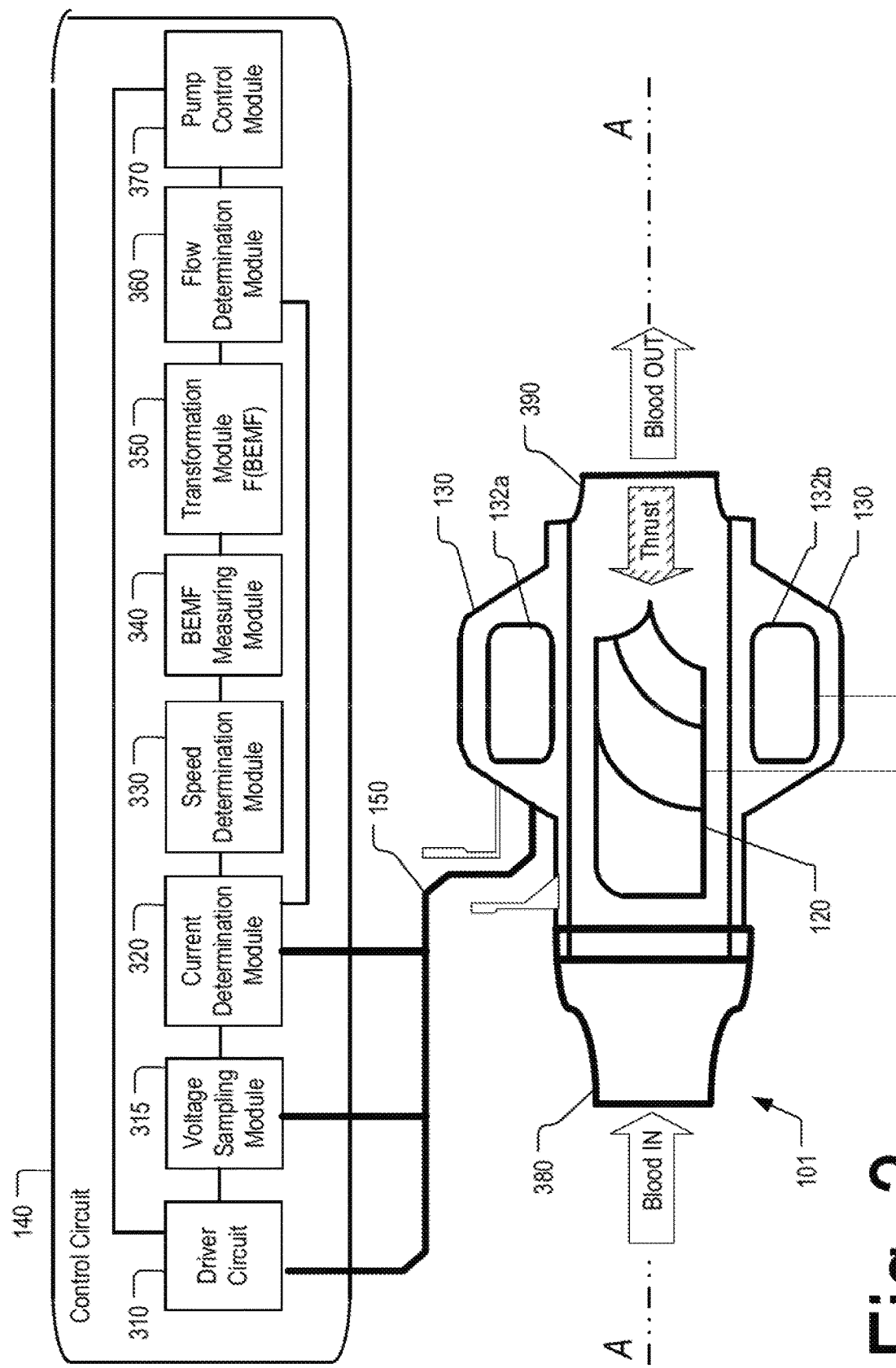
FIG. 3 is a partially functional block diagrammatic, partially sectional view of the blood pump system of FIG. 1.

FIGS. 1-3 depict a blood pump system 100 in accordance with one embodiment of the invention. The blood pump system 100 according to this embodiment includes a control circuit 140 connected via a cable feed 150 to a blood pump 101. The blood pump 101 includes a housing 110 defining a bore 112 having an axis A. A rotor 120 is disposed within the bore. The rotor 120 has a permanent magnetization with flux direction perpendicular to the axis of the bore. The rotor constitutes an impeller configured to push blood in a downstream direction D parallel to the bore 112 when the rotor is turning.

The pump also includes a stator 130. The stator includes coils 132a-e (FIG. 2) connected in a WYE or delta configuration and placed around the circumference of the housing 110. The coils are arranged in pairs diametrically opposed to one another. Thus, coils 132a and 132b form one pair, coils 132c and 132d form another pair, and coils 132e and 132f form another pair. When the coils are driven using a 3-phase current, they provide a magnetic field directed transverse to the bore axis and which rotates around the axis. The magnetic field will interact with the magnetic field of the rotor 120 causing the rotor to turn. In operation, the rotor 120 may be suspended within the bore 112 by magnetic forces, hydrodynamic forces, or both in combination. Desirably, these forces support the rotor so that it does not contact housing 110 during normal operation. Further details about suspended-rotor blood pumps, such as the pump 101, are provided in U.S. Published Patent Application No. 20070100196, entitled "Axial Flow Pump with Multi-Grooved Rotor," the disclosure of which is incorporated herein by reference.

The control circuit 140 comprises driver circuit 310, current determination module 320, and speed determination module 330. BEMF measuring module 340, transformation module 350, flow determination module 360, and pump control module 370. The modules are depicted and discussed with reference to their individual functions. One or more of the modules 310-270 may be implemented using software operating in a computer system including a general-purpose or special purpose processor, in digital circuitry, or in using analog circuitry.

The driver circuit 310 is an electrical circuit for powering the pump 101 with a 3-phase current. Each phase of the three-phase current preferably is in the form of a generally rectangular wave including alternating off or "open-phase" periods in which power is not applied by the drive circuit and on or "closed-phase" periods during which power is applied. The periods of the various phases are arranged so that at any moment, two pairs of coils are on or closed-phase and one pair is off or open-phase. The open-phase and closed-phase periods of the various phases are arranged so that the various pairs of coils go to an open-phase state in sequence, thus creating the rotating magnetic field that actuates the rotor. Driver circuit 310 applies pulse width modulation during each on or closed-phase period. Thus, during each on or closed-phased period, the voltage applied to the pair of coils varies repeatedly between zero and a selected maximum value at a pulse modulation or chopping frequency much higher than the frequency of the rectangular waveform of the repeating closed-phase and open-phase period.

Figure 4:
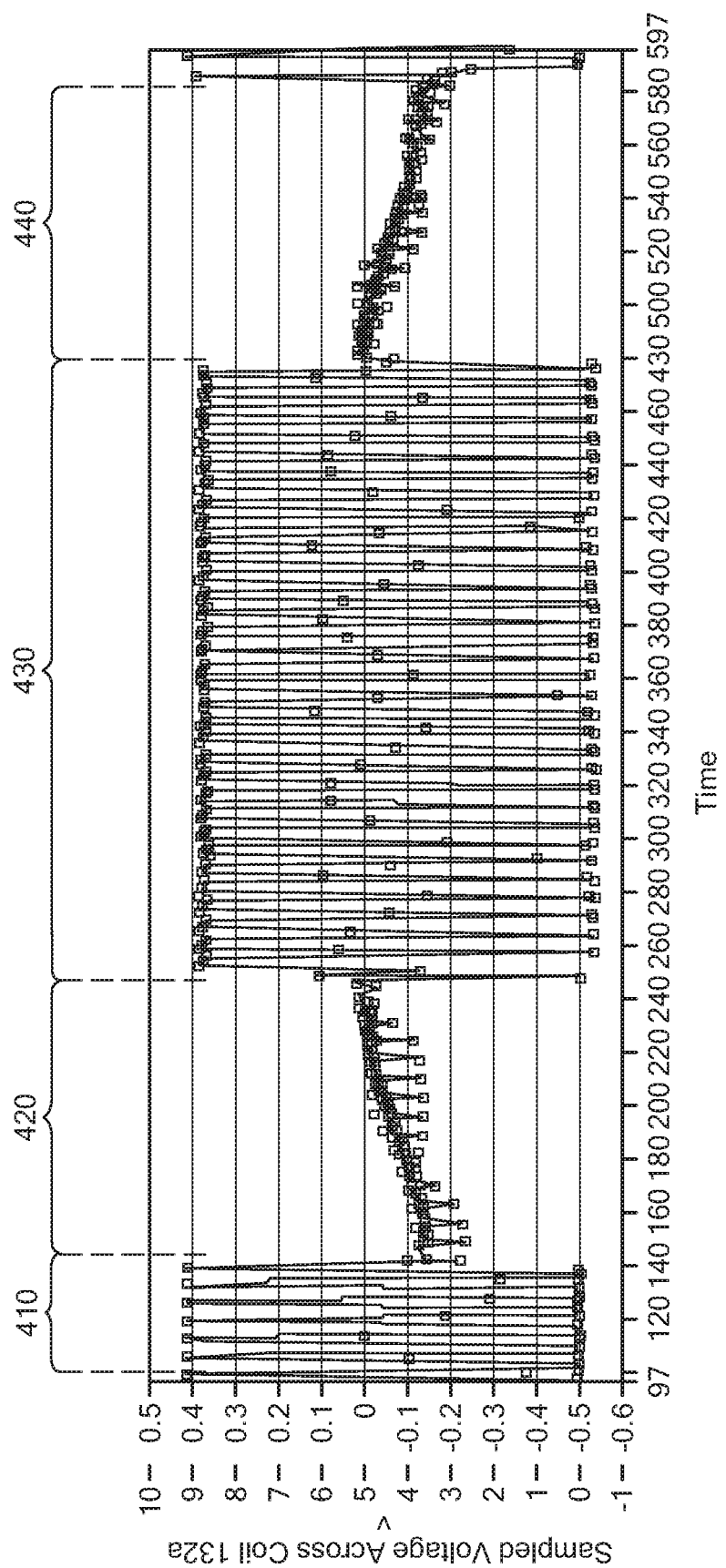
FIG. 4 depicts a plot of voltage sampled across a coil in a stator of the blood pump of FIGS. 1-3.

For example, FIG. 4 depicts the voltage across coil pair 132*a* and 132*b*. During each on or closed-phase period 410 and 430, the voltage applied by the drive circuit is repeatedly chopped or pulse-width modulated. During open-phase periods 420 and 440, the coils 132*a* and 132*b* are not energized by the driver circuit 310. During the open-phase periods, a relatively small voltage appears across coils 132*a* and 132*b*. This voltage is composed primarily of voltage induced in the coil pair 132*a* and 132*b* by the rotating magnetic rotor 120. This induced voltage is referred to as the back electromagnetic force of "BEMF." The BEMF varies in a generally sinusoidal manner; the open periods correspond to the zero-crossings of the sinusoidal variation. The voltage appearing on the coil pair during the open periods also includes some higher-frequency components representing voltage induced in pair 132*a* and 132*b* by the fluctuating pulse-width modulated currents in the other coil which are in the closed-phase or on state. During the open periods 420 and 440, the voltage across coil pair 132*a* and 132*b* is less than a given threshold (e.g., +/−0.5V).

Returning to FIG. 3, the current determination module 320 may include hardware and/or software for determining the amount of current supplied to the pump 101. For example, the current determination module may include a known resistance in series with coil pair 132*a* and 132*b*, and an analog-to-digital converter arranged to sample the voltage across the known resistance so that each such sample represents the instantaneous current passing through the coil pair, as well as an averaging circuit arranged to average these samples to provide a measure of the average current passing through the coil pair.

The control circuit further includes a voltage sampling circuit 315. The voltage-sampling circuit may include an analog-to-digital converter connected across coil pair 132*a* and 132*b* and arranged to capture successive samples of the voltage appearing across the coil pair. The voltage-sampling circuit may also include a digital filter for suppressing variations in the sampled voltage at frequencies at or above the pulse-width modulation or chopping frequency used by the drive circuit, so as to provide a filtered series of values. Alternatively, the sampling circuit may include an analog low-pass filter connected between the analog-to-digital converter and the coil pair.

A speed determination module 330 is operatively connected to the sampling circuit 315 to receive the filtered values from sampling circuit. The speed determination module is arranged to deduce the speed of rotation of the magnetic field, and hence the speed of rotation of rotor 120, from these values. For example, the speed determination module may be arranged to record the time when the voltage on coil pair 132*a* and 132*b* drops below the threshold value associated with the open-phase periods as the beginning of an open-phase period, and to calculate the interval between the beginnings of successive open-phase periods. The speed of rotation is inversely proportional to this time.

The BEMF measuring module 340 is also connected to receive the stream of sampled voltage values from sampling circuit 315, and to record the filtered voltage values during the open-phase periods. These filtered values represent the BEMF generated by the pump. Transformation module 350 is connected to BEMF measuring module 340. The transformation module processes the data collected by the BEMF measuring module 340 to determine a value of a function of the BEMF. The function is referred to herein as F(BEMF). F(BEMF) may be rate of change of the BEMF with respect to time during each open-phase period, i.e., the absolute value of the slope of the BEMF versus time. Like the BEMF measuring module 340, the transformation module 350 may also be implemented using hardware and/or software.

The flow determination module 360 may include hardware and/or software for determining the rate at which blood is impelled by the pump 101. The flow determination module is operatively connected to current determination module 320, speed determination module 330 and transformation module 350 so that the flow determination module 360 receives values representing current, speed and F(BEMF). The flow determination module is arranged to determine the flow rate from the pump based on this information as further discussed below. Pump control module 370 is operatively linked to flow determination module 360 so that the pump control module 370 receives values representing the flow rate from the flow determination module. The pump control module is also linked to driver circuit 310. The pump control module is arranged to determine a desired pump speed based, at least in part, on the flow rate and to command driver circuit 310 accordingly. Thus, the pump control module can control the pump 100 based on the blood flow rate determined by the flow determination module 370 as further discussed below.

In operation, the control circuit 140 powers the pump 101, via the driver circuit 310, thereby causing the rotor 120 to spin. As the rotor 120 spins, blood enters the pump 101 through the inflow end 380 after which the blood is impelled by the rotor 120 from the outflow end 390. As the blood passes through the pump 101, it imparts a thrust on the rotor 120. The magnitude of this thrust is related to the flow rate of blood through the pump.

As discussed above, the rotor 120 is held in position by magnetic and hydrodynamic forces. However, these forces do not hold the rotor with infinite rigidity. Therefore, thrust imparted to the rotor 120 causes the rotor 120 to move by a displacement distance D towards the inflow end 380. For at least some range of thrust values, distance D is related to the magnitude of the thrust and, thus, related to the blood flow rate. Distance D is greatly exaggerated in FIG. 3 for clarity of illustration; in practice, distance D is small in comparison to the dimension of the rotor and pump. Axial displacement of rotor 120 also changes the alignment between the rotor and the coils 132 of the pump. This alters the magnetic interaction between the rotor and the coils of the stator, and thus alters the BEMF. The effect of this alteration will depend, inter alia, on the alignment between the rotor and the coils under zero-thrust conditions and on the configuration of the rotor and the coils. However, for any particular pump operating at a particular speed with blood of a particular viscosity, the effect is repeatable and predictable. The relationship between BEMF and flow rate at one pump speed and blood viscosity for the pump of FIGS. 1-3 is shown by curve 620 in FIG. 6. In the particular embodiment of FIGS. 1-3, the BEMF increases with increasing blood flow rate at least in the range between zero and a flow rate T. Although the present invention is not limited by any theory of operation, it is believed the thrust on the rotor is a composite of reaction components directed upstream toward the inlet end of the pump and viscous components directed downstream toward the outlet end. At zero flow, the reaction components predominate and thus the thrust is directed upstream. As the flow rate increases from zero, the viscous components increase and thus the magnitude of the thrust decreases. As the thrust decreases, distance D decreases and the rotor moves into better alignment with the coils, so that BEMF increases.

Figure 6:
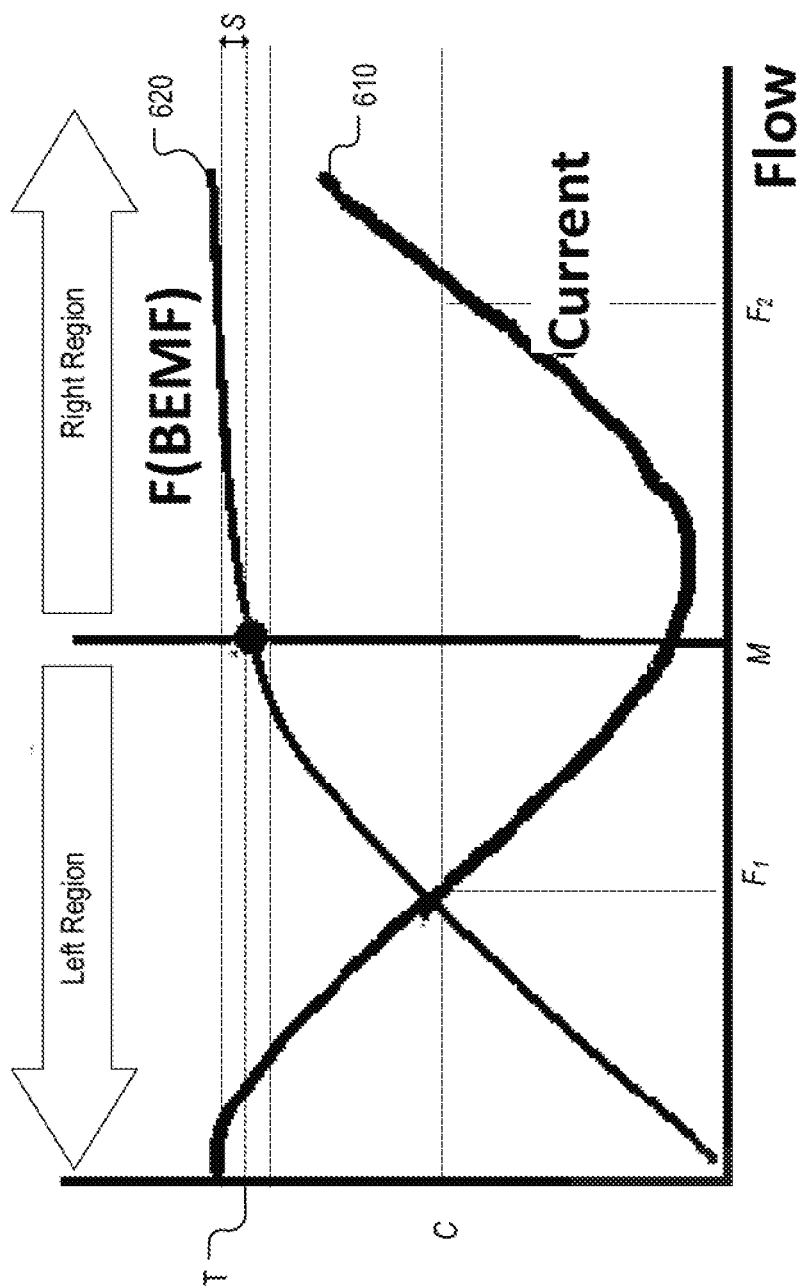
FIG. 6 is a graph depicting certain relationships in operation of the blood pump system of FIGS. 1-3.

Because F(BEMF) (the rate of change in BEMF in the open phase period) is proportional to BEMF, the same curve 620 depicts the relationship between F(BEMF) and the blood flow rate. Stated another way, F(BEMF) is a parameter related to the thrust on the rotor. The flow determination module 360 determines the flow rate of blood through the pump based in part on this parameter as further explained below. As also shown in FIG. 6, the current consumed by the pump also varies with flow rate. Curve 610 depicts the variation of current with flow rate at a particular pump operating speed. The flow determination module 360 uses both current and F(BEMF) to determine the flow rate. In brief, the flow determination module uses the value of F(BEMF) and the relationship between F(BEMF) and flow rate to derive an initial estimate of flow rate. If this initial estimate indicates that the flow rate is significantly below a value M referred to herein as the "fiducial" flow value, the flow determination module uses the value of current and the relationship between current and flow rate indicated in the left region of curve 610 to determine the flow rate. If the initial estimate of flow rate indicates that the flow rate is significantly above the fiducial value M, the flow determination module uses the value of the current and the relationship between current and flow rate indicated in the right region of curve 610 to determine the flow rate. If the initial estimate of flow rate indicates that the flow rate is neither significantly above nor significantly below the fiducial value M, such that there is a degree of uncertainty as to which of the left and right regions of curve 610 should be used to determine the flow rate, the flow determination module uses a combination of flow rates determined from the left and right regions of curve 610 to determine the flow rate.

Figure 5:
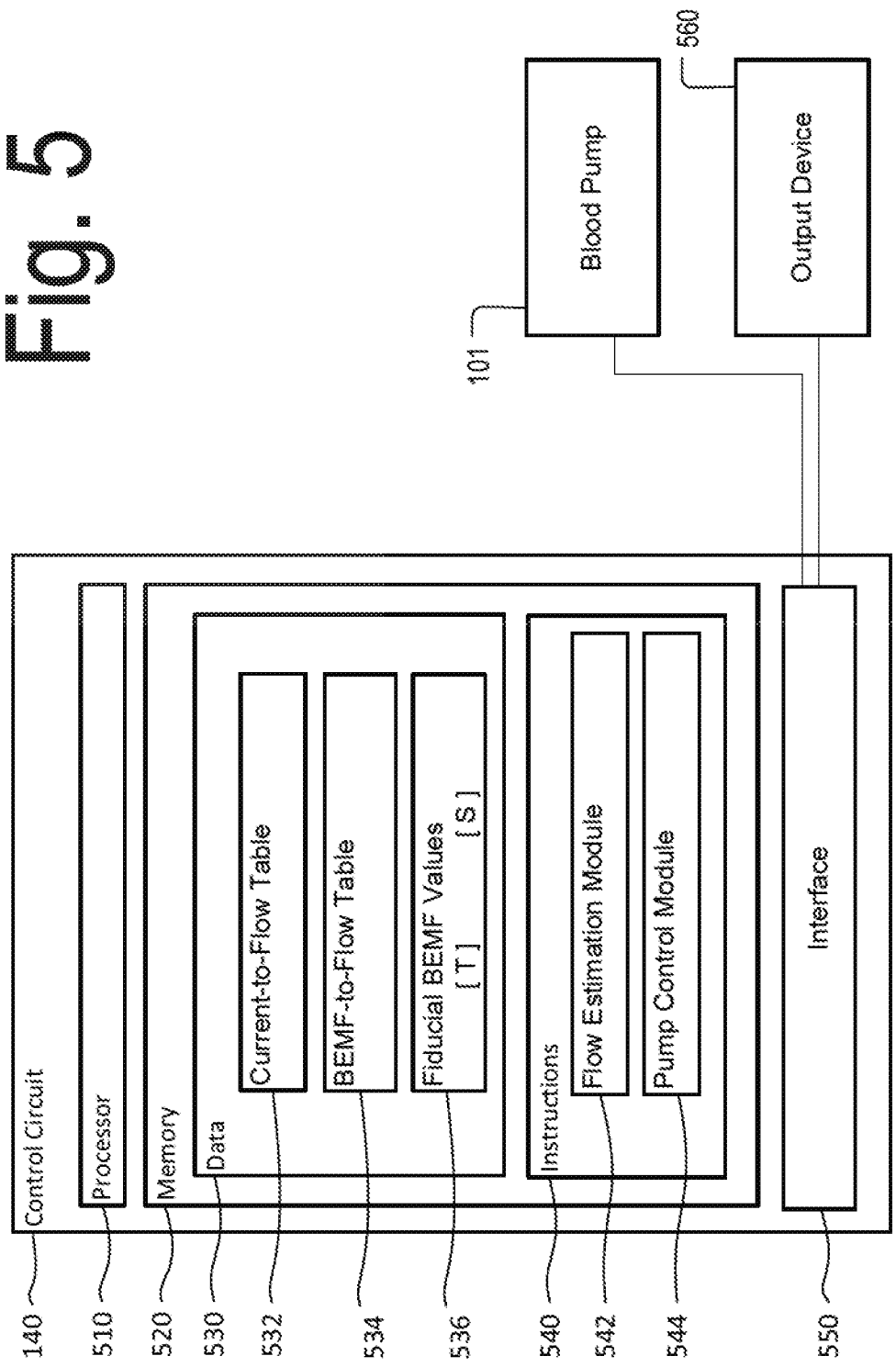
FIG. 5 is a schematic diagram showing the hardware and software used in the blood pump system of FIG. 1-3.

The various modules discussed above with reference to FIG. 3 desirably are implemented at least in part by a general-purpose processor which performs functions associated with the various modules. FIG. 5 depicts this implementation. As shown, the control circuit 140 is implemented using a processor 510, a memory 520, data 530, instructions 540, and an interface 550. Memory 520 stores information accessible by processor 510, including instructions 540 that may be executed by the processor 510. The memory also includes data 530 that may be retrieved, manipulated or stored by the processor. The memory may be of any type capable of storing information accessible by the processor, such as a hard-drive, memory card, ROM, RAM, DVD, CD-ROM, write-capable, and read-only memories. The processor 510 may be any well-known processor, such as commercially available processors. Alternatively, the processor may be a dedicated controller such as an ASIC.

Data 530 may be retrieved, stored or modified by processor 510 in accordance with the instructions 540. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

A current-to-flow table 532 is a tabular representation of the function 610 depicted in FIG. 6. The current-to-flow table 532 may identify one or more blood flow rates that result when a given amount of current is used to power the pump 101. An example of a current-to flow table 532 is provided as Table 1. As shown in FIG. 6, the relationship 610 between current and flow is not a single-valued function. Curve 610 illustrates, for instance, that when C amperes are used to power the pump 101, the pump 101 may impel blood at either $F_1$, L/min or $F_2$, 2 L/min. In other words, the plot illustrates that in this embodiment, there is a many-to-one mapping between current and blood flow rate. As also shown by curve 610, the relationship is such that for any flow in the left region of the current-to-flow relationship, below the fiducial value M liters/minute, there is a one-to-one mapping between current and flow. At any flow above the fiducial value M liters/minute, there is a different one-to-one mapping between current and flow.

Thus, as depicted in Table 1, the current-to-flow map stores plural values of flow rate for each value of current, one associated with the left region and one associated with the right region. At a value of current corresponding to the fiducial flow rate (1.0 amps in the example of Table I), the two values are the same; the current-to-flow table 532 indicates that when the pump 101 is powered with 1.0 amps of current, it pumps blood at the rate of 2 L/min. At a current of 1.2 amps, the blood flow rate is either 1.5 L/min or 3.0 L/min. The current-to-flow relationship varies with the speed of operation of the pump, i.e., the rotation rate of the rotor. The current-to-flow relationship also varies with viscosity of the blood. The viscosity of the blood is directly related to the hematocrit, i.e., the proportion of the blood volume occupied by red blood cells. Therefore, the current-to-flow table stores different sets of values, each associated with a range a particular pump operating speed and blood viscosity. Sets of values for other pump operating speeds and viscosities are calculated from the stored sets by interpolation. The flow calculation module selects the appropriate set of values based on the speed of operation of the pump and on a value of hematocrit or blood viscosity for the patient which has been supplied to the system from an external source through interface 550. The current-to-flow table 532 may be implemented as a file, a data structure, as part of a database, or in any other suitable form.

TABLE 1

| Current-to-Flow Map | | |
|---|---|---|
| Current Flow Rate | Blood Flow Rate Left Region | Blood Flow Rate Right Region |
| 1.0 amps | 2.0 L/min | 2.0 L/min |
| 1.2 amps | 1.5 L/min | 3.0 L/min |
| 1.4 amps | 1.0 L/min | 4.0 L/min |

F(BEMF)-to-flow table 534 may be a tabular representation of the function 620 depicted in FIG. 6. The F(BEMF)-to-flow table 534 identifies the flow rate of blood impelled by the pump 101 when the F(BEMF) indicates that the BEMF in coil pair 132a and 132b changes at a given rate with respect to time. The BEMF-to-flow relationship also changes with pump operating speed and viscosity, i.e., hematocrit. Therefore, table 534 includes different sets of data, each associated with a given speed of rotation of the rotor 120 and a given viscosity. Here again, values for pump operating speeds and blood viscosities not represented in the stored data are derived by interpolation.

An example of the F(BEMF)-to flow table 534 is provided as Table 2. According to this example, the BEMF-to-flow table 534 indicates that when the BEMF in the coil 132a changes at the rate of 5.5 V/s, the pump 101 impels blood at the rate of 2.5 L/min. The BEMF-to-flow table 534 may be implemented as a file, a data structure, as part of a database, or in any other suitable form.

TABLE 2

BEMF-to-Flow Map

| F(BMEF) | Blood Flow Rate (@ 10000 rpm) |
|---|---|
| 0.2 V/s | 0.75 L/min |
| 0.4 V/s | 1.5 L/min |
| 0.5 V/s | 2.0 L/min |
| 0.55 V/s | 2.4 L/min |
| 0.60 V/s | 2.5 L/min |

Fiducial BEMF values 536 for a given pump are also included with the data 530. The fiducial BEMF values 536 provide an indication as to whether the flow determination module should use the relationship between current and flow rate indicated in the left region or right region of curve 610 (FIG. 6), as well as a degree of certainty of such indication. The fiducial midpoint T is the value of F(BEMF) that relates to the flow rate in between the left and right regions of curve 610. The fiducial midpoint is centered in a range of F(BEMF) values referred to herein as a fiducial band. The fiducial band covers a range of values of F(BEMF) that are considered to be neither significantly less than or significantly greater than the fiducial midpoint T. Spread S is defined as half of the fiducial band. In other words, spread S equals the absolute difference between the fiducial midpoint T and either of the maximum F(BEMF) value and minimum F(BEMF) value within the fiducial band. As with tables 532 and 534, the fiducial BEMF values 536 may be implemented as a file, a data structure, as part of a database, or in any other suitable form.

The data may be determined experimentally using the actual pump or a sample pump of similar configuration. In addition, each of the tables may be pre-loaded in the memory 520 before the pump 101 is deployed. With respect to the fiducial BEMF values, these values may also be pre-loaded in the memory 520. The pre-loaded values may be subsequently optimized using the optimization protocol described in greater detail below.

The instructions 540 may be instructions to be executed directly (such as machine code) or indirectly (such as scripts) by the processor. In that regard, the terms "instructions," "steps" and "programs" may be used interchangeably herein. The instructions may be stored in object code format for direct processing by the processor, or in any other computer language including scripts or collections of independent source code modules that are interpreted on demand or compiled in advance. Functions, methods and routines of the instructions are explained in more detail below. Flow estimation module 542 may include instructions for determining the blood flow rate produced by the pump 101 as further explained below, whereas pump control module 544 may include instructions for controlling the operation of the drive circuit 310 (FIG. 3) and thus controlling pump 101. The operations according to instructions 540 is further discussed below with respect to FIG. 7.

The control circuit 140 may optionally include an interface 550 which connects the control circuit 140 to an output device 560. The interface 550 may be an analog interface (e.g., audio interface) or a digital interface, such as Bluetooth. TCP/IP, 3G, and others. Where the control circuit is implemented in an implantable structure adapted to be disposed within the body of the patient, the interface 550 may include known elements for communicating signals through the skin of the patient. The output device 560, may be a speaker, a communications terminal (e.g., computer, cell phone) or any other type of device.

Although FIG. 5 functionally illustrates the processor and memory as being within the same block, it will be understood that the processor and memory may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel.

Figure 7:
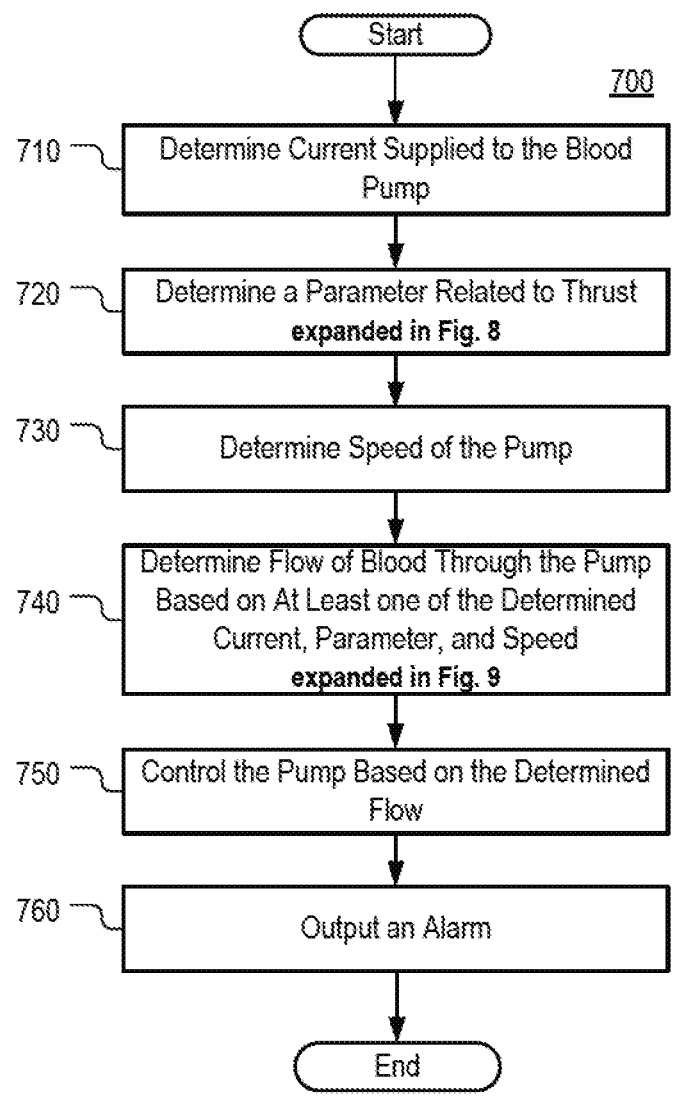
FIG. 7 depicts a flowchart of a method of operation used by the system of FIGS. 1-3.

FIG. 7 depicts a flowchart of a process 700 for determining the rate at which blood is impelled by the pump 101. At task 710, the control circuit 140 determines the amount of current that is used to power the pump 101.

Figure 8:
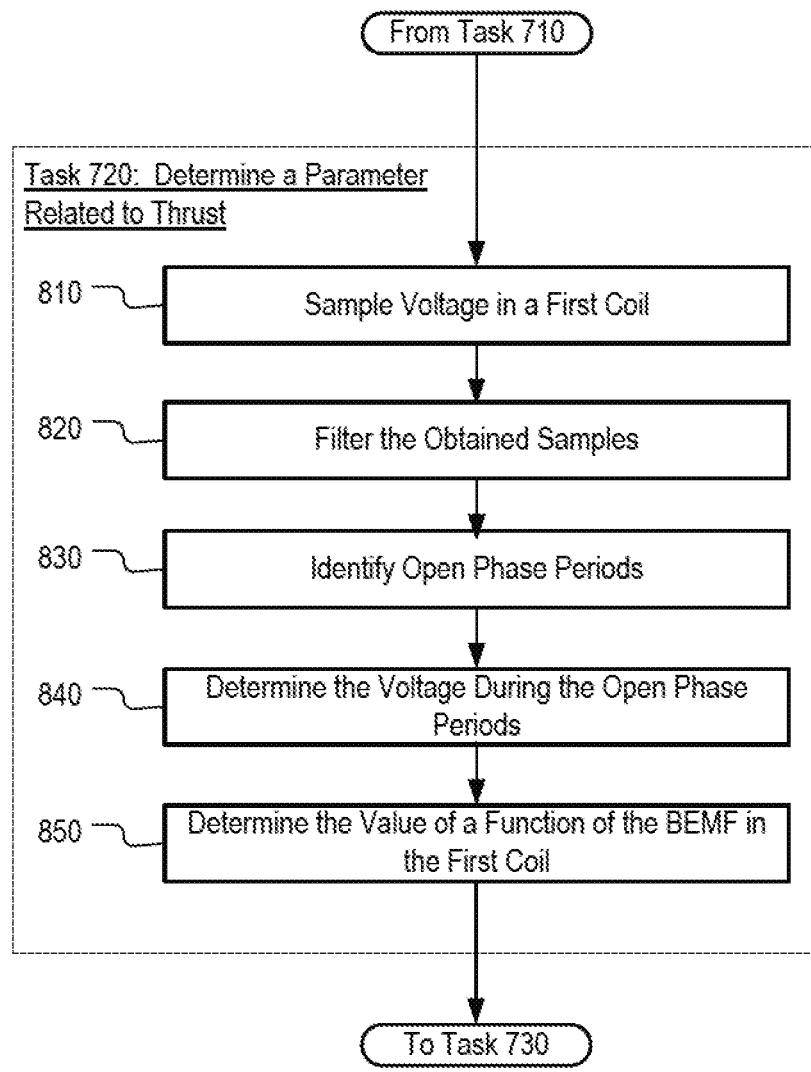
FIGS. 8 and 9 are detail flowchart depicting portions of the method FIG. 7.

At task 720, the control circuit determines a parameter related to thrust imparted on the rotor 120 by the flow of blood exiting the pump 101. In this embodiment, the determined parameter is the function F(BEMF), the rate of change of BEMF during the open phase periods of coil pair 132a and 132b as discussed above. FIG. 8 depicts the sub-steps of step 720. To determine the F(BEMF), the control circuit 140 first samples voltage across the coil pair 132a and 132(b). In one embodiment, for example, the sampling frequency may be 200 kHz (task 810). The samples may then be filtered using an average filter. For example, the filter may be specified as Vout[i]=K*Vin[i]+(1−K)*Vout[i−1], where 0≤K≤1 (task 820). The control circuit 140 then identifies an open phase period. In some aspects the open-phase period based on the voltage levels of the sampled signal being under a predetermined threshold (task 830). Once one or more open-phase periods are identified, the control circuit 140 determines the voltage across the coil 132a during the identified open-phase periods. The determined voltage is the BEMF (task 840). The control circuit calculates F(BEMF), the rate of change in BEMF from the BEMF values during the open-phase periods (task 850). The rate of change may be measured using any number of voltage samples (e.g., 2, 20, 200) taken at any sampling frequency (e.g., 200 kHz). Desirably, calculation of F(BEMF) occurs in real time.

At task 730, (FIG. 7) the control circuit 140 determines the speed of rotation of the rotor 120. As discussed above the control circuit samples voltage across the coil pair 132a and 132b, identifies open-phase periods in which the voltage appearing across the coil is less than a threshold voltage, and determines the number of the open-phase periods per unit time or, equivalently, the time between successive open-phase periods for a particular coil. The control circuit determines the speed based on this measurement. The greater the number of open-phase periods per unit time, or the lesser the time between successive open-phase periods, the faster the speed.

At task 740, the control circuit 140 determines the rate at which blood is impelled by the pump 101 based on the parameter related to thrust determined at task 720.

Figure 9:
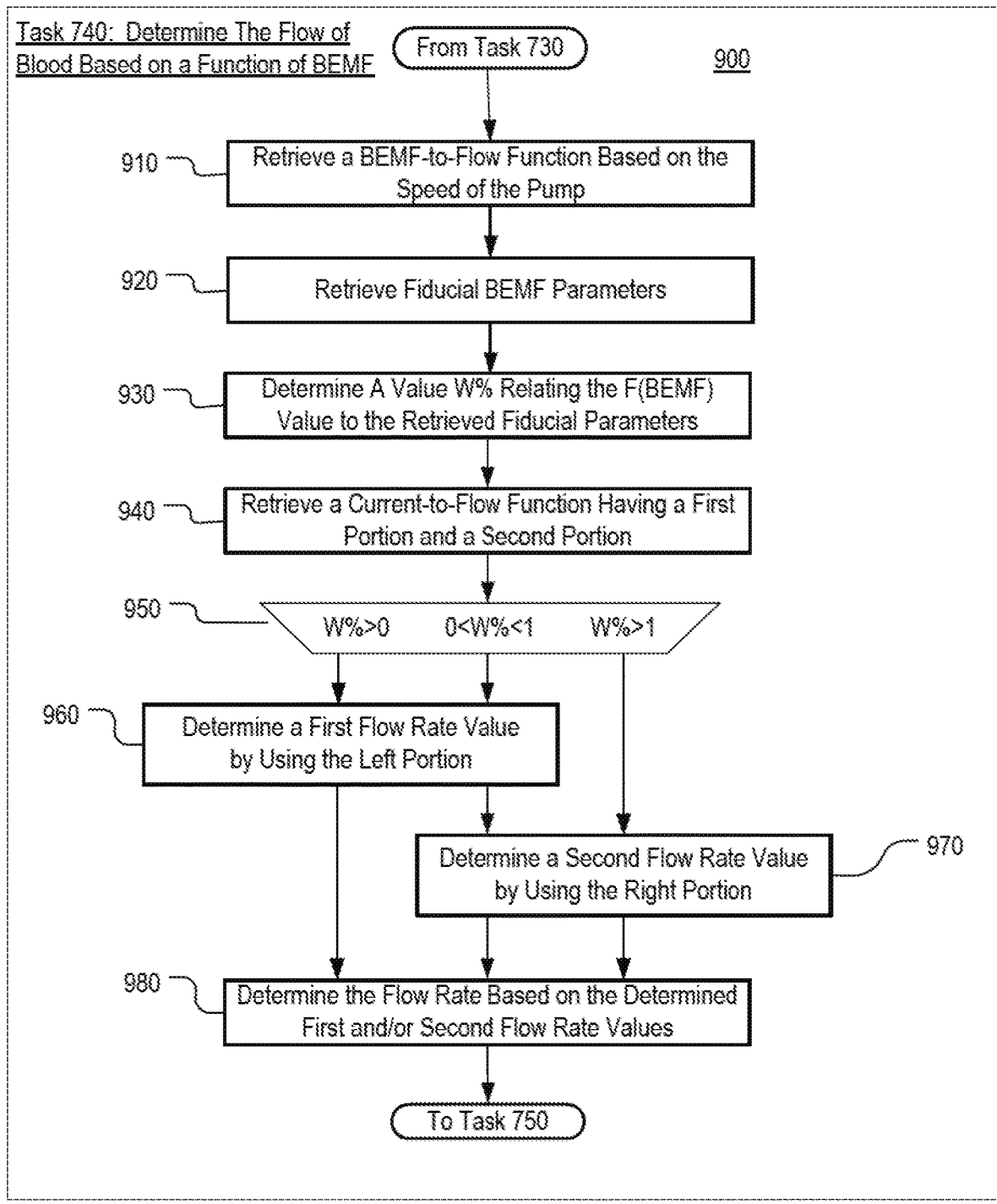

The tasks included in task 740 are shown in greater detail in FIG. 9. At task 910, the control terminal retrieves a function that maps the BEMF slope to a blood flow rate, i.e., F(BEMF)-to-flow table 534 (FIG. 5 and Table II, above), for the speed at which the pump is operating. At task 920, the control circuit 140 retrieves one or more parameters that define the relationship between the determined F(BEMF) and a fiducial value M of flow rate, i.e., fiducial BEMF parameters 536 (FIG. 5). At task 930, the control circuit 140 determines the relative weight W % assigned to each of the left and right blood flow rate values of the current-to-flow table (FIG. 5 and Table I, above). The weight of a flow rate value provided in the current-to-flow table is in part based on the relative certainty that the pump is operating on the left or right region of curve 610. This relative certainty may be calculated using the following formula:

$$W\% = \frac{F(BEMF) - (T - S)}{2S}$$ Formula 1 where F(BEMF) is the value of F(BEMF) determined in task 720, and T and S are the respective fiducial BEMF values 536. Depending on the relationship between the BEMF value, T and S, W % may equal more than 1, less than 0, or between 0 and 1. For example, for values of F(BEMF) that exceed than the range of values within the fiducial band, W % equals more than 1. For values of BEMF that are less than the range of values within the fiducial band, W % is less than 0. For values of F(BEMF) within the fiducial band, W % equals between 0 and 1, and increases linearly proportionately with F(BEMF).

At task 940, the control circuit 140 retrieves the function 610 that maps an amount of current supplied to the pump 101 to blood flow rate that is generated by the pump 101, i.e., the current-to-flow table 532 (FIG. 5 and Table 1, above).

At task 950, the control circuit 140 determines which of two different tasks to execute based on the value of W %. The first task 960 determines a first blood flow rate value based on the left portion of the function 610. The second task 970 determines a second blood flow rate value based on the right portion of the function 610. These tasks 960 and 970 are described in greater detail below. A value of W % that is less than 0 indicates with relative certainty that the correct blood flow rate value is on the left portion of the function 610; therefore, only task 960 is executed by the control circuit. A value of W % that is greater than 1 indicates with relative certainty that the correct blood flow rate value is on the right portion of the function 610; therefore, only task 970 is executed by the control circuit. A value of W % that is between 0 and 1 indicates that the correct blood flow rate value may be either on the left or on the right portion of the function 610; therefore, both tasks 960 and 970 are executed.

At task 960, in order to determine a first blood flow rate value based on the left portion of the function 610, the control circuit 140 may use the value of current as an index and retrieve the corresponding value of flow from the entries in the current-to-flow table 532 (and Table 1, above) that pertains to the left portion. Alternatively, the control circuit 140 may obtain two or more values that correspond to the same amount of current and then select the smallest one. In either process, standard interpolation techniques can be used when the value of current falls between stored values.

At task 970, in order to determine a second blood flow rate value based on the right portion of the function 610, the control circuit 140 may use the value of current as an index and retrieve the corresponding value of flow from the entries in the current-to-flow table 532 (and Table 1, above) that pertain to the right portion. Alternatively, the control circuit 140 may obtain two or more values that correspond to the same amount of current and then select the largest one. In either process, standard interpolation techniques can be used when the value of current falls between stored values.

$$Q_T = [(1 - W\%)*Q_1] + [W\%*Q_2]$$ Formula 2:

where $Q_1$ is the first blood flow rate value (task 960) and $Q_2$ is the second blood flow rate value (task 970), to determine $Q_T$, which is the determined flow rate (task 980). In the example of Formula 2, the control circuit may use fuzzy logic to weigh the first and second blood flow rate values against one another. The weights attributed to both $Q_1$ and $Q_2$ are adjusted proportionate to the value of W % (inversely linearly for $Q_1$, linearly for $Q_2$). Thus, $Q_1$ is attributed a greater weight than $Q_2$ for values of F(BEMF) that are less than T (but greater than T−S), and $Q_2$ is attributed a greater weight than $Q_1$ for values of F(BEMF) that are greater than T (but less than T+S).

The above calculations for determining flow rate are meant as an example and may performed in any particular order or dividing into any number of steps. For instance, the control circuit 140 may first compare F(BEMF) to an absolute difference between T and S (|T−S|). When |T−S| is greater than F(BEMF), W % percent is either greater than 1 (for values of S greater than T) or less than 0 (for values of T greater than S). Under such circumstances, the control circuit may proceed with either task 760 (for T>S) or task 770 (for S>T) without calculating W % or $Q_T$. Otherwise, the control circuit performs both task 760 and 770, and calculates W % and $Q_T$.

At task 750 (FIG. 7), the control circuit 140 controls the operation of the pump 101 or takes other action in response to the determined flow rate. For example, the control circuit may maintain a set point for the flow rate and a moving average of the flow rates as determined over a preset period as, for example, a few minutes. The flow rate set point may be a fixed value or a value determined on the basis of physiological parameters such as the patient's heart rate, respiratory rate or blood oxygen level. If a new value of flow rate is below the moving average by more than a predetermined amount, this may indicate either that the pump has created a suction condition at the intake, or that the outlet of the pump is blocked. For example, where the pump is drawing blood from the left ventricle, a suction condition may arise where the intake of the pump is positioned so that as the heart beats, the opening of the intake comes to rest against the wall of the ventricle and the opening is blocked. In this situation, the flow rate may fluctuate as the beating motion of the heart periodically blocks and unblocks the intake. By contrast, where the outlet of the pump is blocked, the flow rate typically will remain at a low value without such fluctuations. The control circuit can differentiate between such a suction condition and a continual blockage of the pump.

The determined flow rate may also, or alternatively, be used to optimize the pre-loaded fiducial F(BEMF) values for the fiducial midpoint and spread. Often, the pre-loaded fiducial F(BEMF) values are estimates determined during development of the pump. These estimates may be further improved or optimized by comparing a flow rate derived using the pre-loaded values (e.g., the flow rate determined using task 980 of FIG. 9) to a corresponding measured flow rate, such as a flow rate measured by an ultrasonic flow meter. The difference between the derived flow rate and the measured flow rate corresponds to an error in the pre-loaded values. The pre-loaded values may then be adjusted, such as by increasing or decreasing T and/or increasing or decreasing S, in order to reduce the error. The process of deriving a flow value based on the then-current fiducial F(BEMF) values, comparing that value to a measured flow rate value, and updating the fiducial F(BEMF) values may be repeatedly performed until the error is minimized or maintained at a minimum value. The error may be considered minimized or at a minimum value when the estimated flow is within ±1.5 LPM of the measured flow. In one such example, the pump may be considered optimized when the error is considered minimized for one or more of the speeds of the operation of the pump. In another example, the optimization process may be implemented using multiple pumps, with mean F(BEMF) values being acquired from each of the pumps at one or more of the speeds of operation. All of the pumps may be considered optimized when the error for each pump lies inside a predefined tolerance interval (e.g., ±1.5 LPM). The outcome of reducing the error would be an optimized flow estimation algorithm.

A blood pump system 1000 in accordance with yet another embodiment of the invention incorporates an active control system comprising an active control module which exerts an axial force on the rotor to counteract the effects of thrust on the rotor and maintain the rotor in a substantially constant axial position. Further examples of active control systems are provided in U.S. Published Patent Application No. 20110237863, entitled "Magnetically Levitated Blood Pump With Optimization Method Enabling Miniaturization."

Figure 10:
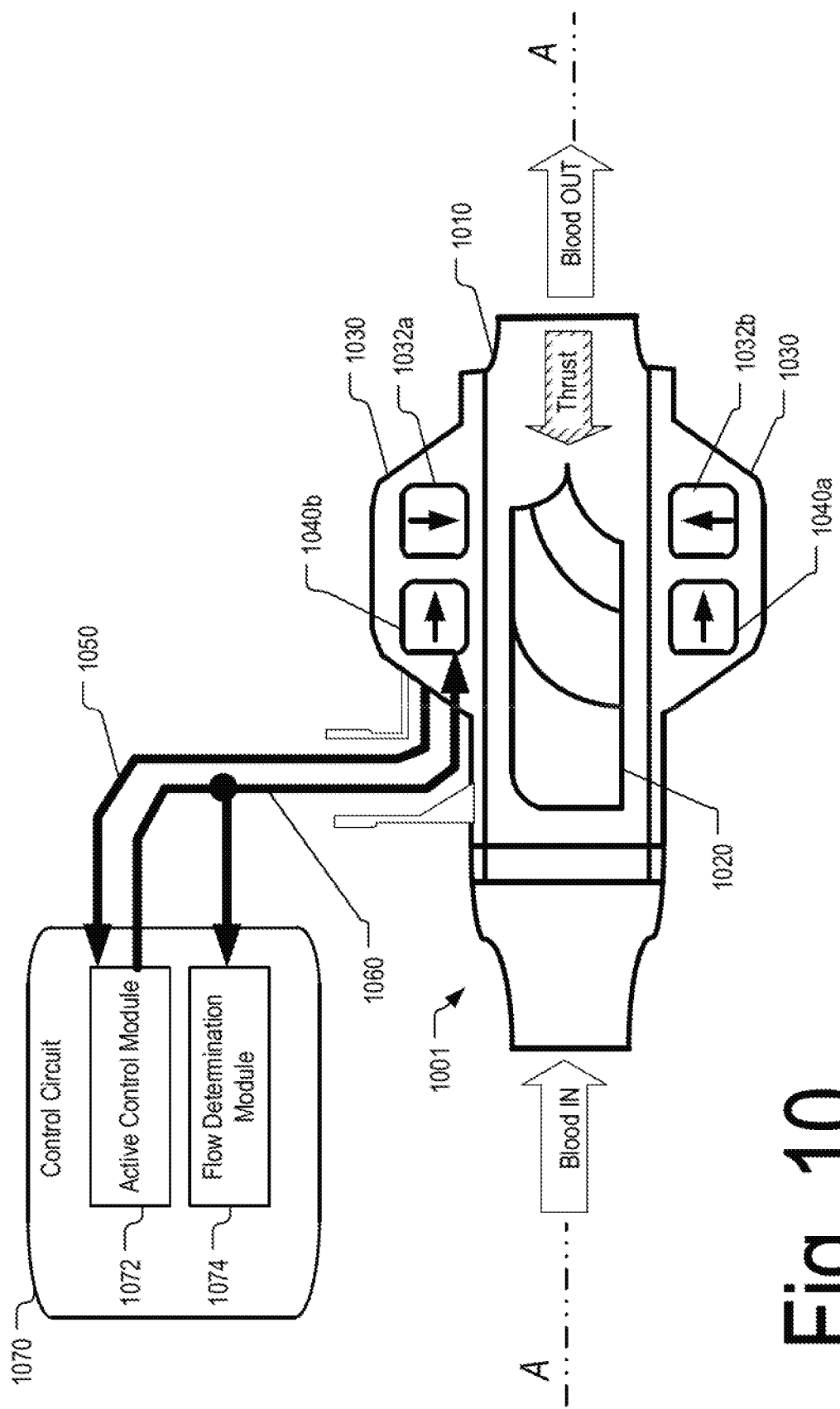
FIG. 10 is a partial block diagrammatic, partial sectional view of a blood pump system in accordance with another embodiment of the invention.

System 1000 comprises a pump 1001 and control circuit 1070. The pump 1001 comprises a rotor 1020 disposed within housing 1010 and actuated by a stator 1030. The rotor 1020 comprises coils 1030. Unlike the pump 101 (FIG. 1), the pump 1001 (FIG. 10) also comprises electromagnets 1040*a-b* for producing a magnetic field which exerts an axial force on rotor 1020 that is opposite in direction and similar in magnitude to the thrust imparted on the rotor 1020 by the flow of blood impelled by the pump 1001. The force produced by the electromagnets balances out the thrust and allows the rotor 1020 to remain in place.

Control circuit 1070 may include an active control module 1072 and flow determination module 1070. The active control module 1072 may receive input signal(s) 1050 and outputs control signal(s) 1060. In this example, the control signal 1060 controls the magnitude of the magnetic field produced by at least one of the electromagnets 1040*a-b*. The control signal 1060 may be a digital directed to a controller that operates the electromagnets 1040*a-b*, an analog current used to power the electromagnets 1040*a-b*, or any other signal. Because the control signal 1060 sets the magnitude of the magnetic field of the electromagnets 1040*a-b*, which is used to offset the thrust imparted on the rotor 100 by the flow of blood output by the pump 101, the control signal 1060 bears a direct relationship to the thrust.

The signal 1060 constitutes another example of a parameter related to thrust and it may be used to determine blood flow rate. The flow determination module 1074 may determine the blood flow rate produced by the pump 1001 by receiving the control signal 1060 and matching it to a corresponding blood flow rate. For example, a table may be stored in a memory of the control circuit 140 that relates different values for the control signals 1040 to blood flow rate. Here again, the table may include different sets of data for different pump operating speeds and blood viscosities. The flow determination module 1074 may use the table to match the value of the control signal 1060 to a corresponding blood flow rate.

In still other arrangements, thrust can be measured directly. For example, if the pump includes a bearing which retains the rotor against axial movement, the bearing may incorporate a piezoelectric element or other force transducer. The signal from the force transducer, or a function of the signal, may be used as the parameter related to thrust.

In the embodiment discussed above with reference to FIGS. 1-9, the parameter F(BEMF) related to thrust is used to select a portion of the current-to-flow relationship 610 (FIG. 6), i.e., the left or right portion of the curve. In a variant of this approach, the system can determine flow directly from F(BEMF) using the F(BEMF)-to-flow table 534 (FIG. 5 and Table 2, above) whenever the value of F(BEMF) is below the fiducial midpoint T, and determine the flow based on the right portion of the current-to-flow relationship 610 when F(BEMF) is above the fiducial midpoint T. In one such variant, the first blood flow rate value (task 960) may be determined directly from F(BEMF), and the second blood flow rate value (task 970) may be determined from the right portion of curve 610. The blood flow rates determined from F(BEMF) and the right portion of curve 610 may then be combined (task 980). In another variant, each of three blood flow rate values may be determined: (1) directly from F(BEMF); (2) from the left portion of curve 610; and (3) from the right portion of curve 610. These three values may then be combined (e.g., first averaging values 1 and 2, and then averaging the first average with value 3 using Formula 2) to determine the blood flow rate of the pump.

As a further alternative, the system can limit determinations of flow directly from F(BEMF) to circumstances in which the value of BEMF is significantly less than the fiducial midpoint T (i.e., less than T−S). As another alternative, the system can further limit determinations of flow directly from F(BEMF) to circumstances in which: (i) the value of BEMF is significantly less than the fiducial midpoint T; and (ii) the speed of rotation of rotor 120 (e.g., determined by the speed determination module 330) is less than 18 kRPM.

In the particular system discussed above with reference to FIGS. 1-9, the relationship between F(BEMF) and flow is such that for values above the threshold, the slope of curve 620 becomes relatively small. In this region, a large change in flow corresponds to only a small change in F(BEMF). This makes it difficult to determine the flow accurately from F(BEMF). However, in other systems having different rotor and coil configurations, the relationship between F(BEMF) and flow provides more substantial variation of F(BEMF) per unit change in flow rate over the entire range of flow rates to be monitored. In those cases, the flow rate can be determined based solely on F(BEMF), without reference to the current used by the pump. Likewise, where another parameter related to thrust is employed, the determination of flow rate can be based solely on such other parameter. In yet another alternative, a parameter related to thrust, such as F(BEMF), can be used without use of the current-to-flow relationship even where the parameter is useful over only a limited range of flow rates. For example, using the same F(BEMF) as employed in FIGS. 1-9, the system can detect occlusion or suction events by comparing the value of F(BEMF) with a relatively low threshold, well below the fiducial midpoint T in FIG. 6. In this arrangement, F(BEMF) is used as a parameter for control or monitoring of the pump without converting it to a value of flow rate. For example, the system may be arranged simply to issue an alarm signal, or take some other predetermined action, whenever F(BEMF) falls below a threshold or remains below the threshold for a particular time. Similar strategies can be used with other parameters related to thrust. In another variant, the system can evaluate the flow rate associated with F(BEMF) and compare that value to a low threshold, below the normal operating range of flow rates.

The control circuit 140 need not store relationships between a parameter such as F(BEMF) and flow or between current and flow in the form of lookup tables as discussed above. The control circuit may retrieve and evaluate a formula that models the rate at which blood is impelled by the pump as a function of the parameter related to thrust, e.g., a formula for the function 620 (FIG. 6). Likewise, the control circuit may retrieve and evaluate a formula for the current-to-flow relationship, e.g., a formula of the function 610.

In the embodiments discussed above, the flow rate determined by the control circuit is used to control the operation of the pump. In other embodiments, the control circuit may simply determine the flow rate and send a signal representing the flow rate to an external device, and may not control operation of the pump.

FIGS. 7-9 are provided as examples. At least some of the tasks associated with FIGS. 7-9 may be performed in a different order than represented, performed concurrently or altogether omitted.

In the embodiment discussed above in connection with FIGS. 6-9, computation of flow rate is based on a weighting parameter that is a particular function of BEMF, namely the rate of change or slope of the BEMF during open phase periods. However, other functions of BEMF may be used as a weighting parameter. For example, the function of BEMF may be simply the magnitude of BEMF detected. Stated another way, as used in this disclosure the expression "function of BEMF" includes BEMF itself as well as other functions of BEMF. Use of a function of BEMF as a parameter for flow rate determination is particularly advantageous because it is not necessary to incorporate any additional transducer into the pump. In effect, the coils of the pump act as the transducer to measure BEMF and thus measuring displacement of the rotor and, indirectly, measuring thrust on the rotor.

Other parameters related to thrust on the rotor may be employed instead of a function of BEMF. For example, where the pump is equipped with a transducer other than the coils which can directly measure the axial position of the rotor, control circuit 140 may determine the flow rate based in whole or in part on a signal from the transducer which represents displacement. Stated another way, the displacement is a parameter related to thrust on the rotor. Any other parameter related to thrust on the rotor can be used.

More generally, while the above embodiments use a weighting parameter related to thrust on the rotor to determine a blood flow rate of a pump, any parameter that increases or decreases monotonically over the range of operable flow rates for the pump may be used. In other words, as long as a parameter is a monotonic function of operable flow rates for the pump, that parameter may be used to make a determination as to whether the pump is operating on the left or right portion of curve 610 and/or a relative certainty of that determination. Furthermore, any parameter that increases or decreases monotonically over even a subset of the range of operable flow rates for the pump may be used. For example, if the parameter is a monotonic function of flow rates for which there is uncertainty whether the pump is operating on the left or right portion of curve 610, that parameter may be used at least to determine the relative certainty of whether the pump is operating on the left or right portion.

Further aspects of this disclosure are described in the disclosure titled "Fiducial Point Optimization," which is attached.

As these and other variations and combinations of the features discussed above can be utilized without departing from the subject matter as defined by the claims, the foregoing description of exemplary aspects should be taken by way of illustration rather than by way of limitation of the subject matter as defined by the claims. It will also be understood that the provision of the examples described herein (as well as clauses phrased as "such as," "e.g.," "including" and the like) should not be interpreted as limiting the claimed subject matter to the specific examples; rather, the examples are intended to illustrate only some of many possible aspects.

What is claimed is:

1. A method for monitoring operation of an implantable blood pump, the method comprising:
   determining an amount of current supplied to the pump;
   determining a first flow rate value and a second flow rate value based on the amount of current supplied to the pump; and
   determining a flow rate of blood based on a combination of the first and second flow rate values and a weighting parameter; and
   assigning to at least one from the group consisting of the first and second flow rate values a weight based at least in part on a determined relationship between the weighting parameter and a predetermined threshold value.

2. The method of claim 1, wherein the implantable blood pump includes a housing having an axis and a rotor disposed within the housing and rotatable around the axis, and wherein the weighting parameter is related to thrust on the rotor along the axis.

3. The method of claim 1, wherein the weighting parameter at least one of increases and decreases monotonically over the range of operable flow rates for the pump.

4. The method of claim 1, wherein the assigned weight for the first flow rate value is inversely proportionate to the relationship between the weighting parameter and the predetermined threshold value, and the assigned weight for the second flow rate value is proportionate to the relationship between the weighting parameter and the predetermined threshold value.

5. The method of claim 1, further comprising:
   calculating an absolute difference between the weighting parameter and a predetermined threshold value;
   comparing said absolute difference to a predetermined spread value; and
   wherein the flow rate of blood based is determined based on a combination of the first and second flow rate values when the absolute difference between the third parameter and a predetermined threshold value is less than the predetermined spread value.

6. The method of claim 5, further comprising:
   determining a speed of rotation of the rotor; and
   comparing the determined speed to a threshold value, wherein when absolute difference is greater than the predetermined spread value, the third parameter is less than the predetermined threshold value:
the flow rate of blood is determined based on the first flow rate value when the determined speed is greater than the threshold value, and
when the determined speed is less than the threshold speed value, the flow rate of blood is determined based on the third parameter and neither of the first and second flow rate values.

7. A control circuit for monitoring the operation of an implantable blood pump, the control circuit comprising:
a current determination circuit configure to determine an amount of current supplied to the pump;
a flow rate value determination circuit configure to determine a first flow rate value and a second flow rate value based on the amount of current supplied to the pump;
a transformation circuit configured to determine a weighting parameter; and
a flow rate determination circuit configure to determine a flow rate of blood through the pump based on a at least one from the group consisting of the first and second flow rate values and the weighting parameter, the flow rate determination circuit being further configured to:
determine a relationship between the weighting parameter and a predetermined threshold value; and
determine a respective weight for each of the first and second flow rate values based on the relationship.

8. The control circuit of claim 7, wherein the implantable blood pump includes a housing having an axis and a rotor disposed within the housing and rotatable around the axis, and wherein the weighting parameter is related to thrust on the rotor along the axis.

9. The control circuit of claim 7, wherein the weight for the first flow rate value is inversely proportionate to the relationship between the weighting parameter and the predetermined threshold value, and the weight for the second flow rate value is proportionate to the relationship between the weighting parameter and a predetermined threshold value.

10. The control circuit of claim 7, wherein the flow rate determination circuit is further operative to:
calculate an absolute difference between the third parameter and a predetermined threshold value; and
compare the absolute difference to a predetermined spread value,
wherein the flow rate determination circuit determines the flow rate of blood based on a combination of the first and second flow rate values when the absolute difference between the third parameter and a predetermined threshold value is less than the predetermined spread value.

11. The control circuit of claim 10, wherein the flow rate determination circuit is further operative to:
determine the flow rate of blood based on the first flow rate value and not the second flow rate value when absolute difference is greater than the spread value, and the weighting parameter is less than the predetermined threshold value; and
determine the flow rate of blood based on the second flow rate value and not the first flow rate value when the absolute difference is greater than a spread value, and the weighting parameter is greater than the predetermined threshold value.

12. A control circuit as in claim 10, further comprising a speed determination circuit operative to determine a speed of rotation of the rotor, wherein the flow rate determination circuit is further operative to:
compare the determined speed to a preselected threshold value;
determine the flow rate of blood based on based on the weighting parameter and neither of the first and second flow rate values when the absolute difference is greater than a spread value, the weighting parameter is less than the predetermined threshold value and the determined speed is less than the threshold value.

* * * * *